United States Patent [19]

Meier

[11] Patent Number: 4,845,305

[45] Date of Patent: Jul. 4, 1989

[54] PROCESS FOR THE PREPARATION OF ISOPHTHALADEHYDE

[75] Inventor: Eric A. Meier, Hamilton Square, N.J.

[73] Assignee: National Starch and Chemical Corporation, Bridgewater, N.J.

[21] Appl. No.: 203,654

[22] Filed: Jul. 7, 1988

[51] Int. Cl.$^4$ .................. C07C 45/00; C07C 47/52
[52] U.S. Cl. ..................... 568/436; 568/433
[58] Field of Search .................. 568/436, 433

[56] References Cited

U.S. PATENT DOCUMENTS 4,206,152  6/1980  Gostel ........................... 568/436
4,465,865  8/1984  Engländer et al. ............. 568/436

OTHER PUBLICATIONS

Johnston, N. W. and Williams, J. L. R., *Journal of the American Chemical Society*, 69, 2065 (1947).
Organic Syntheses, Collective vol. V, pp. 668–669 (1973).
Beilstein's *Hanbuch der Organischen Chemie, Band VII*, p. 675; Abstract Citing.
Liebig's *Annalen der Chemie*, 347, p. 109 (1906).
Angyal, S. J. and Rassack, R. C., *Journal of the Chemical Society*, pp. 2700–2704 (1949).
Vogel's Textbook of Practical Organic Chemistry, 4th Ed., pp. 764–765, Longman Inc., N.Y. (1978).

*Primary Examiner*—J. E. Evans
*Assistant Examiner*—Karen E. Kulesza
*Attorney, Agent, or Firm*—Royal N. Ronning, Jr.; Edwin M. Szala

[57] ABSTRACT

This invention presents a method for the preparation of isophthalaldehyde in an all-aqueous solution using m-xylenediamine, hexamethylenetetramine, and HCl as the only reactants. Such a process permits the preparation of high yield of a high purity product.

15 Claims, No Drawings

PROCESS FOR THE PREPARATION OF ISOPHTHALADEHYDE

BACKGROUND OF INVENTION

Isophthalaldehyde (IPAL) is an intermediate used in the production of many adhesives. It can be produced by a variety of methods, each one having its individual advantages and drawbacks. Some of the principal preparation routes are:

a. Oxidation/hydrolysis of m-xylene

In this synthesis, described by M. W. Johnston and J. L. R. Williams in Journal of the Amer. Chem. Soc., 69 P2065 (1947), m-xylene is subjected to the following reaction:

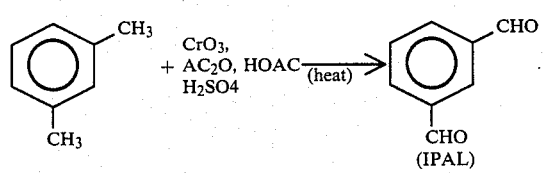

This reaction suffers from the distinct drawbacks of the requirement of costly solvent and reactants and also from the fact that the highly toxic chromous (Cr$^{+3}$) ions are produced in stoichiometric quantities as a reaction by product. Further, the yields realized are quite poor.

b. Bromination of m-xylene followed by hydrolysis

In this synthesis, reported in Liebig's Annalen der Chemie, 347 p. 109 (1906), xylene is brominated to form a geminal dihalide, which is then hydrolysed to form IPAL, as follows:

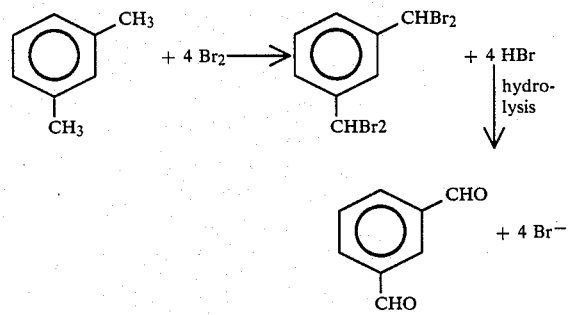

This reaction suffers from the requirement of bromine, a highly corrosive liquid, as a reactant. Further, the toxic bromide ion (br$^-$) is formed in stoichiometric quantities as a reaction byproduct.

c. Catalytic reduction of Isophthaloyl Chloride

In this synthesis, an example of the Rosenmund reduction, an acyl chloride is reduced by hydrogen in the presence of a metallic catalyst as follows:

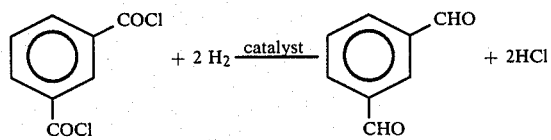

This reaction suffers from the requirment of a corrosive and expensive acyl chloride for a starting material and also from the production of HCl as a reaction by-product.

d. Modified Sommelet Procedure

In this procedure, reported in Organic Syntheses collective vol. V, pp 668-669 (1973), m-xylene diamine and hexamethylene tetramine are reacted in a modified Sommelet procedure as follows:

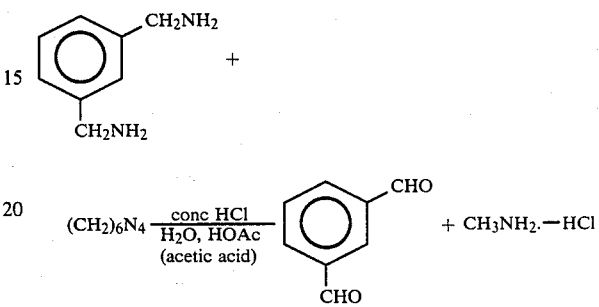

This method requires the use of expensive reagents, including a large amount of glacial acetic acid (which is difficult to recover from the reaction mixture). Further, since the reaction occurs in acid solution, recovery of the IPAL requires a base neutralization prior to recovery.

There exists a real need for a synthetic procedure which overcomes these drawbacks.

SUMMARY OF INVENTION

It is an object of this invention to present a synthetic method for production of IPAL which overcomes the problems observed with previous methods. It is further an object of this invention to present a synthetic method for the production of IPAL which is easily practiced and produces the product in high yield without the need for excessive purification steps.

This invention presents a method for the procudtion of IPAL which satisfies these objects. The method, which is a further modification of the modified Sommelet procedure described supra, comprises reacting m-xylenediamine and hexamethylene tetramine in the presence of aqueous HCl. The HCl is "demand fed" to the reaction mixture to keep the pH at the desired level and, thus, the quantity of acid used can be kept to a minimum. Once the reaction is complete, the product can be recovered by crystallization followed by filtration, or by other separation means. The yield of the process can run as high as 90% or higher.

DETAILED DESCRIPTION OF INVENTION

The method of this invention is a modification of the modified Sommelet procedure described in *Organic Syntheses,* collective vol. V, pp. 668-669 (1973), incorporated herein by reference. Briefly, in the process, m-xylenediamine (XDA) and hexamethylene tetramine are dissolved in an effective amount of water to achieve dissolution. Concentrated HCl is then added with agitation, to bring the reaction mixture to the desired pH. The agitated mixture is then heated to reflux (about 100° C.) and refluxed under an air or water-cooled condenser for a sufficient time to permit the reaction to proceed to completion (about 2-3 hours). During this refluxing the pH is continuously monitored, and HCl is continuously "demand-fed" to maintain the pH at the desired value. The reaction is subsequently discontinued by removing the heat and the product is recovered by standard separation means.

The XDA and HMT are preferentially added in a HMT/XDA molar ration of about 3/1 to about 5/1, more preferably about 3.5/1. Significant departures from this range will still produce usable product, but the yields will be greatly reduced.

The pH of the reacting system is preferentially maintained in the range of 3.0–5.5, preferably 3.4–5.5, more preferably 3.4–4.5 with the lower pH's being preferred. Ideally, the pH of the system is initially brought to about 3.4 (by the addition of concentrated HCl), and then maintained between 3.4 and 4.5 during refluxing by "demand-feeding" of HCl. This will result in about 2–3 moles of HCl to be added for each mole of HMT, preferably 2.6 moles/mole of HMT.

Appropriate control of pH requires continuous monitoring during the entire reaction. This monitoring can be achieved in any convenient way including using a pH meter or a chemical acid/base indicator. Of particular use in this application is the acid/base indicator Bromcresol Green, which exhibits a yellow to blue color change in the pH range 3.4–5.5. It is also noted that the pH ranges presented are the optimal ranges. The reaction will proceed at virtually any acidic pH; however, any significant deviation from these preferred ranges will result in lower yields.

During the course of the reaction HCl is continually "demand-fed" to maintain the pH in the required range. This feeding of HCl can be accomplished manually or by any other convenient means. A particularly useful method of addition involves the use of an automatic titrating system whereby the pH is monitored by a meter and the HCl is automatically added to keep the pH at the desired level.

After reaction, the product is preferentially recovered from solution by crystallyzation at 5° C., although this temperature can be raised and/or lowered between 0° and 10° C. as the application dictates, followed by filtration to recover the crystals. Other recovery means such as distillation, etc. can also be employed. The crude product can then, if desired, be purified by aqueous recrystallization.

The product recovered by crystallization and subjected to one aqueous recrystallization procedure, is typically >99% pure, and the yield is typically 50–90%.

EXAMPLES

Example 1 - Comparative Preparations of IPAL

IPAL was prepared in a 12 liter apparatus using the Modified Sommelet procedure with the following charges. For comparison purposes, the charges for a similar reaction using the method of the instant invention were estimated.

| Reactant | Charge Modified Sommelet | Invention (est.) |
| --- | --- | --- |
| XDA | 272 gm | 272 gm |
| HMTA | 1000 gm | 1000 gm |
| conc. HCl | 480 ml | 1555 ml |
| glacial HOAc (acetic acid) | 1600 ml | — |
| water | 3200 ml | 1600 ml. |
| NaOH | 298 gm | — |
| water | 3850 ml | — |

As shown, it can be seen that the reactants required for equivalent reaction scales (same theoretical yields) are much greater with the Modified Sommelett procedure than with that of the instant invention. In particular, it is noted that the Modified Sommelett procedure requires the use of 1600 ml of glacial acetic acid and 298 gm NaOH, while the method of the instant invention requires neither of these. Since glacial acetic acid is a highly expensive reagent, the cost savings achieved by employing the method of the instant invention are considerable.

Example 2 - Preparation of IPAL by the Modified Sommelet Method

To assess yield and purity, a series of experiments were conducted to prepare IPAL using the Modified Sommelet procedure. Charges to the 12 liter reactor were the same as in Example 1; charges to the smaller (1 liter) or larger (24 liter) reactions were increased or decreased accordingly. The results are presented below.

| Exp. No. | Scale | Yield Crude | Recrystallized* |
| --- | --- | --- | --- |
| 1 | 12 liter | — | 53.8% |
| 2 | 1 liter | 59.3% | — |
| 3 | 24 liter | — | 51.0% |
| 4 | 12 liter | — | 41.0% |
| 5 | 12 liter | — | 45.3% |
| 6 | 12 liter | — | 46.6% |

*Subjected to a single aqueous recrystallization step using 37 gm $H_2O$/gm solid.

The product was typically a white crystalline solid having a melting point of 89°–91° C.

It can be seen that yields were typically less than 50% of theoretical, with the highest yield being 59.3% (in the 1 liter reactor).

Example 3 - Preparation of IPAL by the Method of the Invention

A series of experiments were conducted to prepare IPAL using the method of the instant invention. The first experiment was conducted in a 3 liter reactor using the following charge:

XDA, 122 gm (0.90 moles)
Water, 1440 gm
HMT, 450 gm (3.21 moles)

Concentrated HCl was then added at a constant rate of 10 ml/min. until the pH attained 3.4 as indicated by Bromcresol Green (a total of 826 gm HCl were added to this point).

The system was then refluxed at approximately 100° C. dor 2½ hours, demand feeding conc. HCl to maintain this pH (another 826 gm were added during this time).

The product was then recovered by crystallization at 5° C., and subjected to aqueous recrystallization (to purify) as in Example 2.

Each subsequent experiment was conducted in this manner, proportionally increasing or decreasing the charges as the reactor scale was increased or decreased. Also, the pH monitoring indicators were changed as conditions dictated and in one experiment, a glass electrode pH meter was used.

The results are presented below.

| Exp. No. | Scale | pH | pH measured by | Yield Crude | Yield Recrys. |
|---|---|---|---|---|---|
| 1 | 3 liter | 3.5 | Bromcresol Green | — | 53.8% |
| 2 | 2 liter | 2.4 | Methyl Yellow | 21.9% | — |
| 3 | 2 liter | 3.5 | Bromcresol Green | 72.0% | 51.1% |
| 4 | 1 liter | 3.5 | Bromcresol Green | — | 63.0% |
| 5 | 2 liter | 3.5 | pH meter | 66.5% | — |
| 6 | 2 liter | 3.5 | Bromcresol Green | 91.4% | 73.6% |

The results demonstrate that, at pH 3.5, the yields range from 53.8% 73.6%; at pH 2.4, the yield is significantly reduced. Further, all recrystallized products were analyzed for purity and found to have a melting point of 86°–88° C., and a purity (as measured on a GC/MS) in excess of 99%.

Thus, under optimal conditions of pH, the yields exceed those observed with the Modified Sommelet procedure. The product purity is quite high as evidenced by the GC/MS data.

It is apparent that many variations and modifications of the invention as hereinabove set forth may be made without departing from the spirit and scope thereof. The specific embodiments described are given by way of example only and the invention is limited only by the terms of the appended claims.

What is claimed is:

1. A method for preparing isophthalaldehyde in an aqueous reaction medium comprising:
    (i) dissolving m-xylenediamine and hexamethylene tetramine in an effective amount of water to achieve dissolution;
    (ii) adding to the reaction mixture an effective amount of concentrated hydrochloric acid to achieve a pH of about 3.0 to about 5.5
    (iii) heating the reaction mixture to reflux;
    (iv) refluxing the reaction mixture for about 2 to about 3 hours while continuously demand feeding an effective amount of concentrated hydrochloric acid such that the pH is maintained at about 3.0 to about 5.5; and
    (v) recovering the isophthalaldehyde product.

2. The method of claim 1, wherein the molar ratio of hexamethylenetetramine to m-xylenediamine ranges from about 3/1 to about 5/1.

3. The method of claim 2, wherein the molar ratio of hexamethylenetetramine to m-xylenediamine is about 3.5/1.

4. The method of claim 1, wherein a total of about 2–3 moles of HCl are added to the reaction mixture for each mole of hexamethylene tetramine present in the reaction mixture.

5. The method of claim 4, wherein a total of about 2.6 moles of HCl are added to the reaction mixture for each mole of hexamethylene tetramine present in the reaction mixture.

6. The method of claim 5, wherein the reaction mixture is initially brought to a pH of about 3.4.

7. The method of claim 5, wherein the pH is maintained at about 3.4 to about 5.5 during the refluxing step.

8. The method of claim 1, wherein the pH is monitored voltametrically using a pH meter.

9. The method of claim 1, wherein the pH is monitored chemically by use of a colorimetric acid-base indicator.

10. The method of claim 9, wherein the acid-base indicator is Bromcresol Green.

11. The method of claim 1, wherein the refluxing is continued for about 2.5 hours.

12. The method of claim 1, wherein the refluxing is accomplished by the use of a water-cooled condenser.

13. The method of claim 1, wherein the refluxing is accomplished by the use of an air-cooled condenser.

14. The method of claim 1, wherein the product is recovered by crystallization.

15. The method of claim 14, wherein the recovered product is purified by aqueous recrystallization.

* * * * *